(12) United States Patent
Young et al.

(10) Patent No.: US 8,887,578 B2
(45) Date of Patent: Nov. 18, 2014

(54) CORIOLIS MASS FLOW RATE SENSOR

(71) Applicant: Malema Engineering Corporation, Boca Raton, FL (US)

(72) Inventors: Alan M. Young, Los Gatos, CA (US); Jianren Lin, San Jose, CA (US); Claus W. Knudsen, Fremont, CA (US)

(73) Assignee: Malema Engineering Coproration, Boca Raton, FL (US)

( * ) Notice: Subject to any disclaimer, the term of this patent is extended or adjusted under 35 U.S.C. 154(b) by 0 days.

(21) Appl. No.: 13/768,366

(22) Filed: Feb. 15, 2013

(65) Prior Publication Data

US 2013/0174670 A1 Jul. 11, 2013

Related U.S. Application Data

(62) Division of application No. 12/779,151, filed on May 13, 2010, now Pat. No. 8,404,076.

(60) Provisional application No. 61/304,228, filed on Feb. 12, 2010.

(51) Int. Cl.
*G01F 1/84* (2006.01)
*B29C 67/00* (2006.01)
*G01F 25/00* (2006.01)
*B29K 21/00* (2006.01)

(52) U.S. Cl.
CPC ............ *G01F 1/8477* (2013.01); *B29C 67/004* (2013.01); *G01F 1/8427* (2013.01); *G01F 1/8431* (2013.01); *G01F 1/8436* (2013.01); *G01F 1/8404* (2013.01); *G01F 1/8418* (2013.01); *G01F 25/0007* (2013.01); *B29K 2021/00* (2013.01)
USPC .................................................... 73/861.354

(58) Field of Classification Search
USPC ...................................... 73/861.354–861.357
See application file for complete search history.

(56) References Cited

U.S. PATENT DOCUMENTS

| 5,373,634 | A | 12/1994 | Lipp |
| 6,450,042 | B1 * | 9/2002 | Lanham et al. .......... 73/861.357 |
| 6,662,120 | B2 * | 12/2003 | Drahm et al. .................... 702/43 |
| 6,802,224 | B2 * | 10/2004 | Nakao et al. ............. 73/861.354 |
| 7,350,421 | B2 * | 4/2008 | Anklin-Imhof et al. . 73/861.355 |
| 7,562,585 | B2 * | 7/2009 | Schuetze et al. ......... 73/861.355 |
| 2010/0251830 | A1 * | 10/2010 | Bitto et al. ............... 73/861.357 |

OTHER PUBLICATIONS

Korean Intellectual Property Office, Office Action, Korean Patent Application No. 10-2012-7023722, Jan. 15, 2014, ten pages.
State Intellectual Property Office of the People's Republic of China, First Office Action, Chinese Patent Application No. 201080063688.8, Apr. 4, 2014, six pages.

* cited by examiner

*Primary Examiner* — Jewel V Thompson
(74) *Attorney, Agent, or Firm* — Fenwick & West LLP (57) ABSTRACT

A subassembly of a Coriolis flowmeter is fabricated from a single monolithic piece of elastic polymeric material. The subassembly includes two flow-sensitive members and a base integrally connected to the two flow-sensitive members. The two flow-sensitive members include straight sections, and are substantially similar and parallel to each other. Flow passages are drilled along the straight sections of the two flow-sensitive members, and drilled entrances are sealed using the elastic polymeric material. A temperature sensor is fixedly attached to a flow-sensitive member for measuring a temperature of the flow-sensitive member and communicating the temperature to a metering electronics. The metering electronics determines a calibrated flow rate of fluid flowing through the Coriolis flowmeter that accounts for the temperature.

9 Claims, 8 Drawing Sheets

CORIOLIS MASS FLOW RATE SENSOR

CROSS REFERENCE TO RELATED APPLICATIONS

This application claims the benefit of U.S. Provisional Application No. 61/304,228, "METHODS OF MANUFACTURING AND TEMPERATURE CALIBRATING A CORIOLIS MASS FLOW RATE SENSOR" by Alan M. Young, Jianren Lin, and Claus W. Knudsen, filed on Feb. 12, 2010, and is a divisional application of U.S. patent application Ser. No. 12/779,151, the contents of which are hereby incorporated by reference in their entirety.

FIELD OF THE INVENTION

The present invention relates generally to fluid mass flow rate and density measuring apparatus based on the Coriolis-effect and in particular, methods for fabricating and calibrating an improved Coriolis flow rate sensor constructed from an elastic polymeric material (e.g., PFA—perfluoroalkoxy copolymer).

DESCRIPTION OF PRIOR ART

It is well known that Coriolis mass flowmeters can be used to measure the mass flow rate (as well as other properties) of a fluid flowing through a pipeline. Traditional Coriolis flowmeters employ various configurations of one or two tubes that are oscillated in a controlled manner allowing measurement of Coriolis induced deflections (or the effects of such deflections on the tube(s)) as an indication of fluid mass flow rate flowing through the sensor. As expressed in U.S. Pat. No. 7,127,815 B2 (col. 2, lines 5-25), much of the Coriolis flowmeter prior art is concerned with using metal flow tubes as the flow-sensitive element, but the prior art also suggests that plastic may be substituted for metal. The '815 patent states that "the mere assertion that a flowmeter could be made out of plastic is nothing more than the abstraction that plastic can be substituted for metal. It does not teach how a plastic flowmeter can be manufactured to generate accurate information over a useful range of operating conditions." Similar statements are found in U.S. Pat. No. 6,776,053 B2 (Col. 1, lines 58-68 and Col. 2, lines 1-10).

The '815 and '053 patents describe methods of fabricating a Coriolis flowmeter with at least one PFA tube attached to a metal base using a cyanoacrylate adhesive. Fundamental to the successful operation of any Coriolis flowmeter is that the flow sensitive element (e.g., a tube in the '815 and '053 patents) must be fixedly attached to a metal base (or manifold) in such a manner that a fixed, stable and unchanging boundary condition is established for the ends of the vibrating sensitive element. For example, the '053 patent states in claim 1 (Col. 14, lines 65-67) that ". . . end portions of said flow tube apparatus coupled to said base to create stationary nodes at said end portions . . . ". However, a shortcoming of the '053 and '815 patents is that under normal operating conditions the integrity of the coupling of the tube to the metal base is not necessarily unyielding and unchanging. Rather, it could deteriorate over time from continuous vibration of the tube causing the adhesive joint to crack or otherwise degrade. Additionally, differential thermal expansion/contraction between the different materials of construction (e.g., the tube, the cyanoacrylate adhesive and the metal base) will impair the integrity of the coupling of the tube to the metal base creating an unstable boundary condition resulting in uncontrolled vibration characteristics to such an extent that performance of the device would be compromised.

The '815 and '053 patents describe properties of PFA tubing which, by its method of manufacture (i.e., extrusion) inherently has bends or curvature that must be eliminated prior to manufacturing a flowmeter (e.g., see '815, Col. 3, lines 42-55). According to the '815 and '053 patents, this problem can be alleviated by subjecting the PFA tubing to an annealing process (see '815, col. 3, lines 30-41) in order to straighten the tube prior to fabricating a flowmeter.

To facilitate binding of the cyanoacrylate adhesive to the PFA tube, the tubing must be subjected to etching (a process referred to in the '815 patent) that requires submersing and gently agitating PFA tubes in a heated bath containing glycol diether. However, these annealing and etching processes add cost and complexity to the fabrication of the flowmeter and may not necessarily yield tubing suitable for flowmeter fabrication on a consistent basis.

U.S. Pat. Nos. 6,450,042 B1, 6,904,667 B2 and U.S. Patent Application Publication No. 20020139199 A1 describe methods of fabricating a Coriolis flowmeter via injection molding and forming the flow path from a core mold made from a low-melting point fusible metal alloy containing a mixture of Bismuth, Lead, Tin, Cadmium, and Indium with a melting point of about 47 degrees Celsius. The '042 patent asserts (Col. 2, lines 65-67) that " . . . with the possible exception of a driver and pick offs, and case, the entirety of the flowmeter is formed by injection molding (emphasis added)." However, this method of fabrication presents significant problems and limitations. During the injection molding process, hot plastic is injected into a mold at temperatures that can exceed 350 degrees Celsius at pressures exceeding 5000 psi. When fabricating thin-wall or small diameter flow passageways (e.g., 4 mm diameter; wall thickness <2 mm) such melt temperatures and pressures will likely distort the comparatively narrow (and flexible) fusible metal core (possibly melting its surface) resulting in deformation and contamination of the flow passageways to such an extent that the device could be rendered unusable. In semiconductor, pharmaceutical, bio-pharmaceutical (or other critical high-purity process applications) it is important to avoid metallic contamination however infinitesimal. However, unlike a solid core (e.g., stainless steel), the comparatively soft fusible core could partially melt or abrade during the injection molding process allowing metal atoms to mix and become embedded within the injected plastic permanently contaminating the flow passageway rendering the device unsuitable for high-purity applications.

In plastic injection molding processes, it is generally recommended that molded features have a similar thickness because otherwise the molded part may not form properly. With reference to the '042 patent, this requirement means that all structural features of the Coriolis flowmeters described therein, namely the tube wall, "brace bars", inlet and outlet flanges, manifold walls, . . . etc., must all have a similar thickness. However, a consequence of forming the entirety of the flowmeter by injection molding could result in structural and/or dynamic design limitations or compromises that could adversely affect and/or limit flowmeter performance.

The "spring constant" of a tube material (which is proportional to Youngs Modulus) varies with temperature and directly affects the accuracy of a Coriolis flowmeter. To maintain flow rate measurement accuracy, Coriolis flowmeters require temperature compensation as the fluid and/or ambient temperature changes the temperature of the flow-sensitive element. Youngs Modulus data vs. temperature is available from N.I.S.T. (or other technical references) for most all metal alloys used in the construction of prior art Coriolis flowmeters (e.g., stainless steel or Titanium). However, comparable data (e.g., elastic modulus vs. temperature) for elastic polymers are generally not available or are published at very few temperatures. Hence, prior art suggesting or describing the use of plastic for fabricating a Coriolis flowmeter, which also mention means for sensing the temperature of the flow-sensitive element (e.g., see '815, col. 4, lines 59-67), fail to describe how to implement effective temperature compensation over a range of operating temperatures for any given elastic polymeric material. Significantly, without such temperature compensation, the meter would not be usable in applications wherein the sensor temperature differs substantially from that at calibration.

SUMMARY OF THE PRESENT INVENTION

It is an aspect of the present invention to provide a method of fabricating a Coriolis flowmeter from an elastic polymeric material having flow sensitive element(s) integrally connected to a suitable mounting base (or manifold) of the same material free of mechanical joints or adhesives thereby providing an unyielding, fixed boundary condition for the vibrating sensitive element.

It is another aspect of the present invention to provide a method of fabricating a Coriolis flowmeter from an elastic polymeric material having a flow sensitive element integrally connected to a suitable mounting base (or manifold) of the same material free of adhesives or mechanical joints thereby avoiding differential thermal expansion/contraction that would otherwise undermine the integrity and reliability of the boundary condition at the ends of the vibrating flow sensitive element.

It is another aspect of the present invention to provide a method of fabricating a Coriolis flowmeter from an elastic polymeric material employing a flow sensitive element that does not use tubing thereby avoiding the additional processing steps such as annealing and etching thereby simplifying the flowmeter fabrication process.

It is another aspect of the present invention to provide a method of fabricating a Coriolis flowmeter from an elastic polymeric material and forming a flow sensitive element (and flow passageways therein) without using low-melting point fusible metal alloys that could permanently contaminate the flow passageway(s).

It is another aspect of the present invention to provide a method of fabricating a Coriolis flowmeter from an elastic polymeric material allowing the fabrication of a flow sensitive element with comparatively thin-walls and/or with relatively small diameter flow passageways therein.

It is yet another aspect object of the present invention to provide a method for calibrating a Coriolis flowmeter fabricated from any elastic material (metal or plastic) allowing for accurate temperature compensation of the flow sensitive element's spring constant over any useful operating temperature range of the flowmeter.

Briefly, an embodiment of the present invention includes a structure employing a flow-sensitive element comprising two substantially identical members wherein each member is shaped in the form of a rectangular "U" (or a triangle among other possible shapes that may be fabricated from straight sections) which extend from a support to which they are integrally connected. Fluid flows through each member of the flow-sensitive element in a hydraulically serial (or parallel) fashion via suitable external fluid connections. The "legs" of the flow sensitive members may have circular, oval, rectangular, hexagonal, or octagonal cross-section. The structure is fabricated from a single piece of elastic polymeric material.

The fabrication process involves either CNC (computer numerical control) machining the entire structure from a single piece of polymeric material and drilling the flow passageways as a secondary operation. Alternatively, the structure can be fabricated by injection molding, the flow passageways being formed by a combination of a solid core employed within the mold and/or secondary drilling operations after the part is removed from its mold. These fabrication methods yield a completely functioning (i.e., dynamically responsive) flowmeter after secondary (post-molding) operations. External holes (from coring or drilling) are filled by a suitable secondary procedure (e.g., welding).

These and other objects and advantages of the present invention will no doubt become apparent to those skilled in the art after having read the following detailed description of the various embodiments illustrated in the figures of the drawing.

DETAILED DESCRIPTION

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures and may indicate similar or like functionality.

Figure 1:
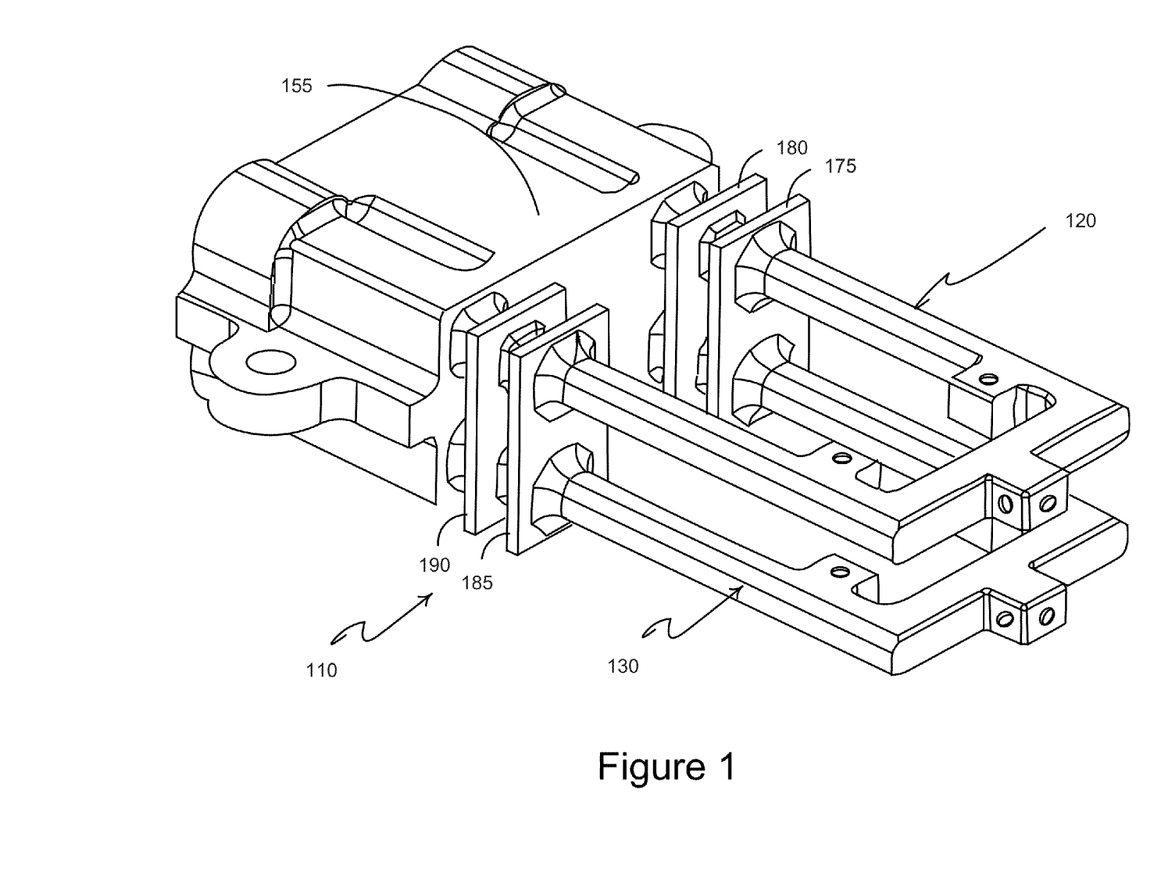
FIG. 1. Illustration of a partially constructed Coriolis flow sensor subassembly fabricated from an elastic polymeric material without internal flow passageways.

FIG. 1 illustrates a solid piece 110 of polymeric material, CNC-machined from a single block of elastic polymeric material, according to one embodiment. The flow-sensitive element of subassembly 110 is comprised of two square "U"-shaped assemblies 120 and 130. However, subassembly 110 is devoid of flow passageways to allow fluid to flow through the structure. Sub-assembly 110 can also be formed by injection molding but, as with the CNC-machined version, without any provision for flow passageways. By the very nature of how structure 110 is fabricated (i.e., CNC machining or injection molding), each "U" is integrally connected to "isolation plates" 175, 180 and 185, 190 (which establish boundary conditions for vibration of the "U"-shaped structures 120 and 130) and, in turn, is integrally connected to support 155. Importantly, subassembly 110 is fabricated as one solid part devoid of mechanical joints, adhesives or without using any metal support.

Figure 2:
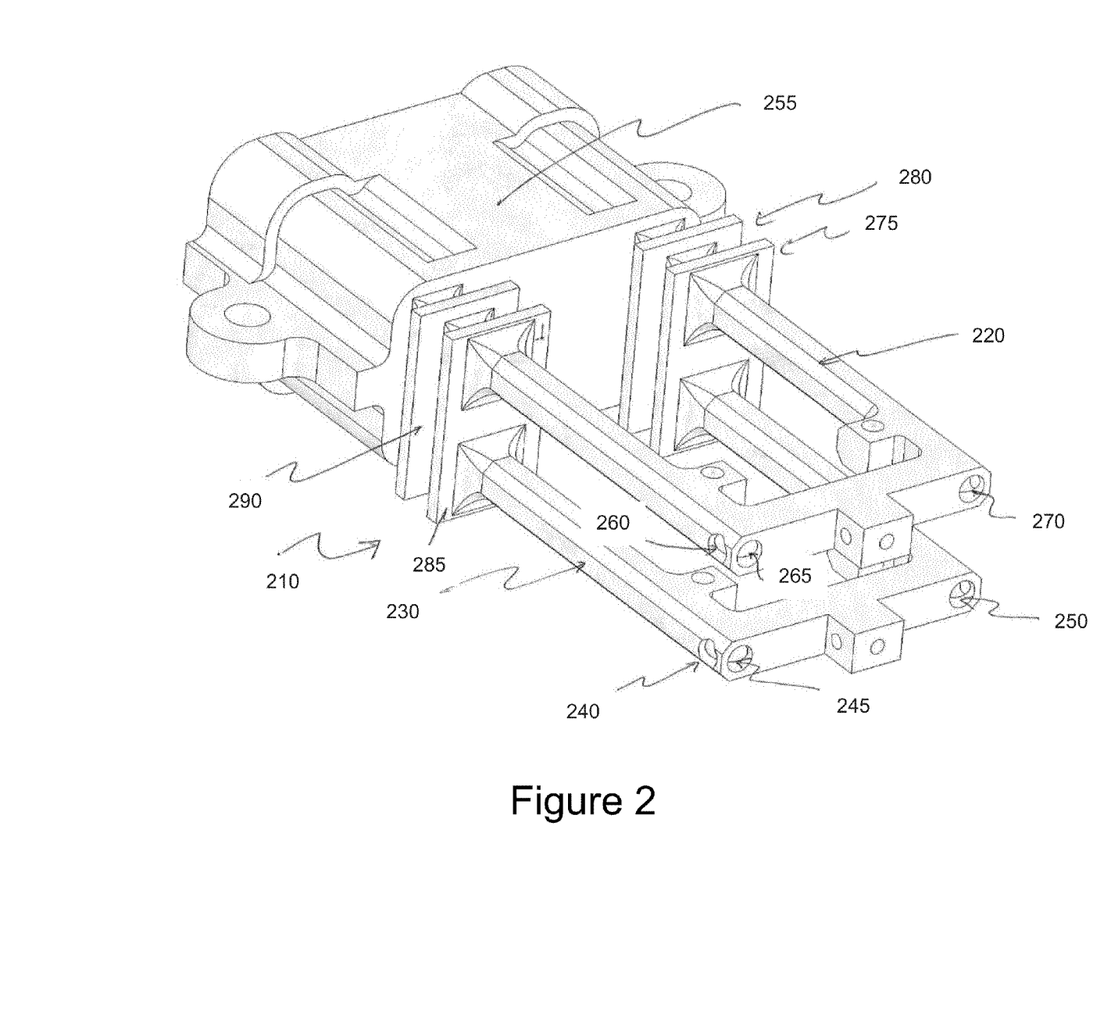
FIG. 2. Illustration of a partially constructed Coriolis flow sensor subassembly fabricated from an elastic polymeric material with internal flow passageways formed by drilling.
Figure 3:
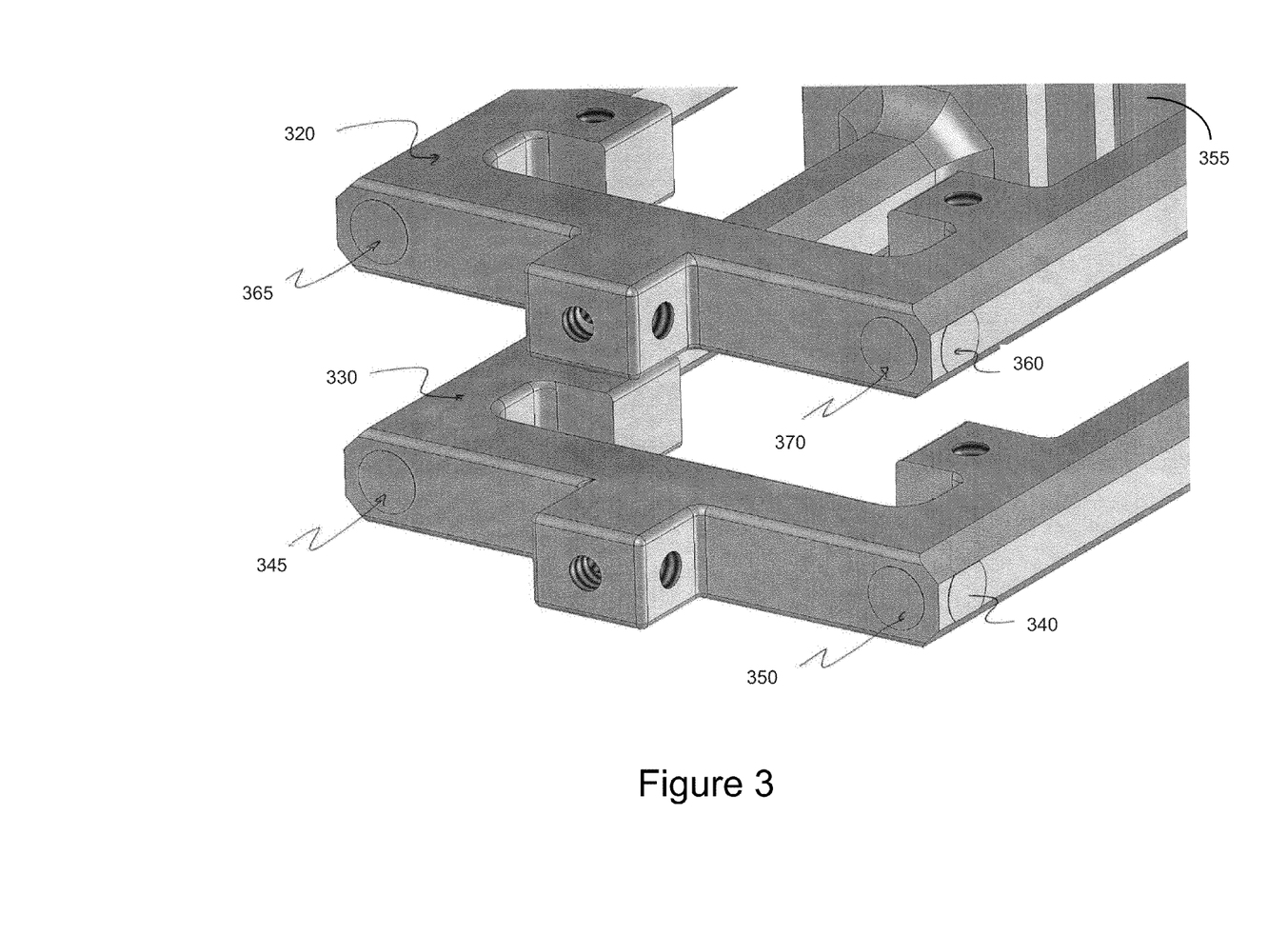
FIG. 3. Illustration of a partially constructed Coriolis flow sensor subassembly fabricated from an elastic polymeric material with sealed drill-holes for internal flow passageways.

FIG. 2 illustrates sub-assembly 210, but with flow passageways 240 and 260 drilled completely end-to-end laterally along the centerline of the "end-section" of each "U", according to one embodiment. Likewise, flow passageways 245, 250, 265 and 270 are drilled completely through along the centerline of the side-legs of each "U" and through to exit the rearmost end of support 255 (not shown). Additionally, according to one embodiment, to complete fabrication of flow channels through each "U", the drilled openings are sealed as illustrated in FIG. 3 wherein each hole at the end "U" is sealed by welding or by melting plastic into the drilled entrances of passageways 340, 345, 350 and 360, 365, 370. According to one embodiment, to prevent blockage of the flow passageways during the sealing or welding operation, a mandrel with a rounded-tip is inserted along the length of each passageway prior to sealing holes allowing the plastic melt to form a smooth surface against the rounded tip of the mandrel thereby preventing internal blockage of the flow passageway. Plumbing connections (not shown) configured at the rear of block 355 allow fluid to flow through each "U" in a hydraulically serial or parallel manner.

Figure 8:
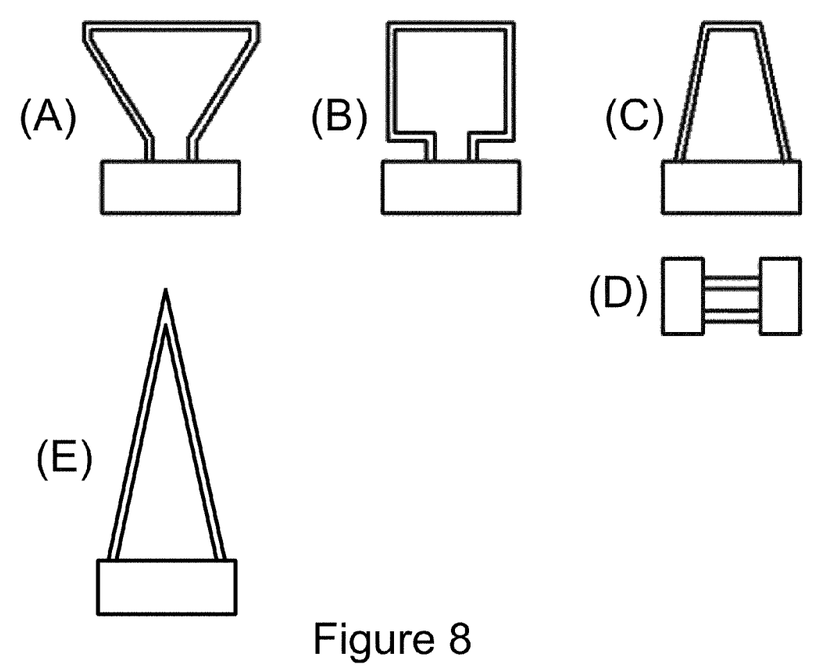
FIG. 8. Illustration of additional embodiments of flow-sensitive elements.

Members of the flow-sensitive element are not limited to the square "U"-shape shown in FIGS. 1 and 2, and can have other shapes that may be fabricated from straight sections. FIG. 8 illustrates five example shapes for the flow-sensitive element members: triangle (options (A) and (E)), square (option (B)), trapezoid (option (C)), and straight line (option (D)).

Figure 4:
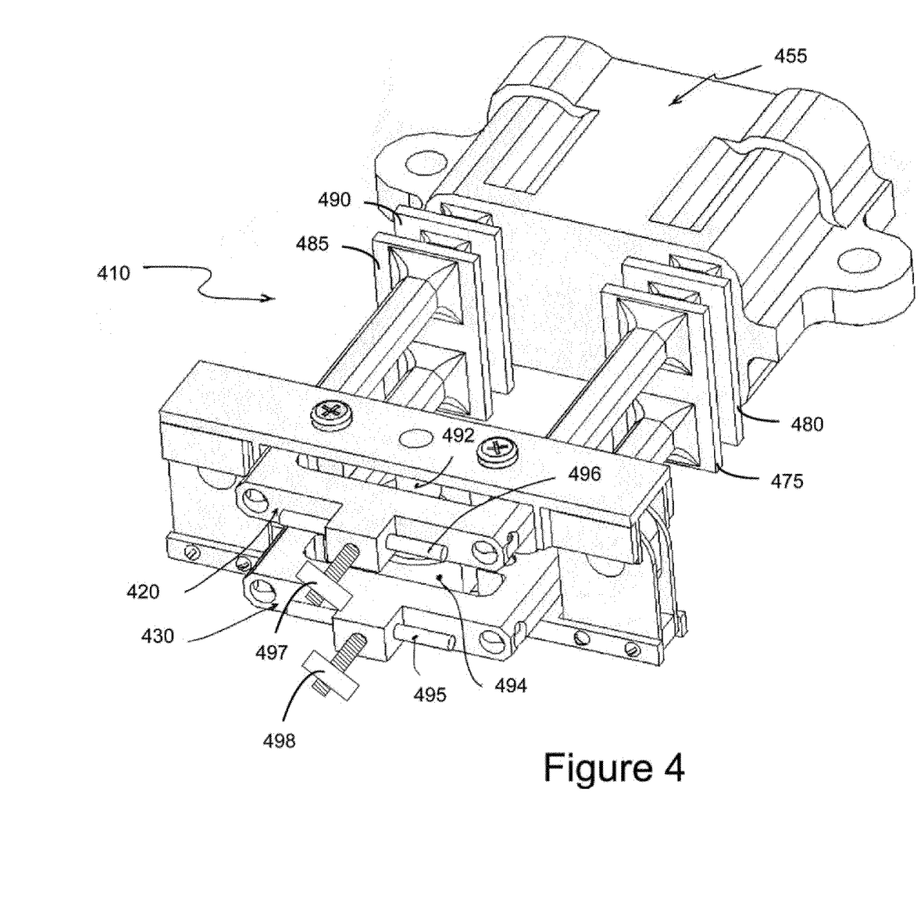
FIG. 4. Illustration of a partially assembled Coriolis flow sensor with excitation magnet-coil assembly and motion-sensing magnet/coil assemblies.

FIG. 4 depicts a subassembly 410 of a Coriolis flowmeter having a pair of sensitive elements 420 and 430 integrally attached to support block 455, according to one embodiment. Fluid material is introduced at the rear of block 455 and is directed to flow in the same direction through each flow sensitive element 420 and 430 in a hydraulically serial or parallel (i.e., split flow) manner. Flow sensitive structures 420 and 430 extend through isolation plates 475, 480, 485, 490 to support block 455. Support block 455, flow sensitive structures 420 and 430 and isolation plates 475, 480, 485, 490 are integrally connected as they are all fabricated from a single monolithic piece of elastic polymeric material.

Figure 5:
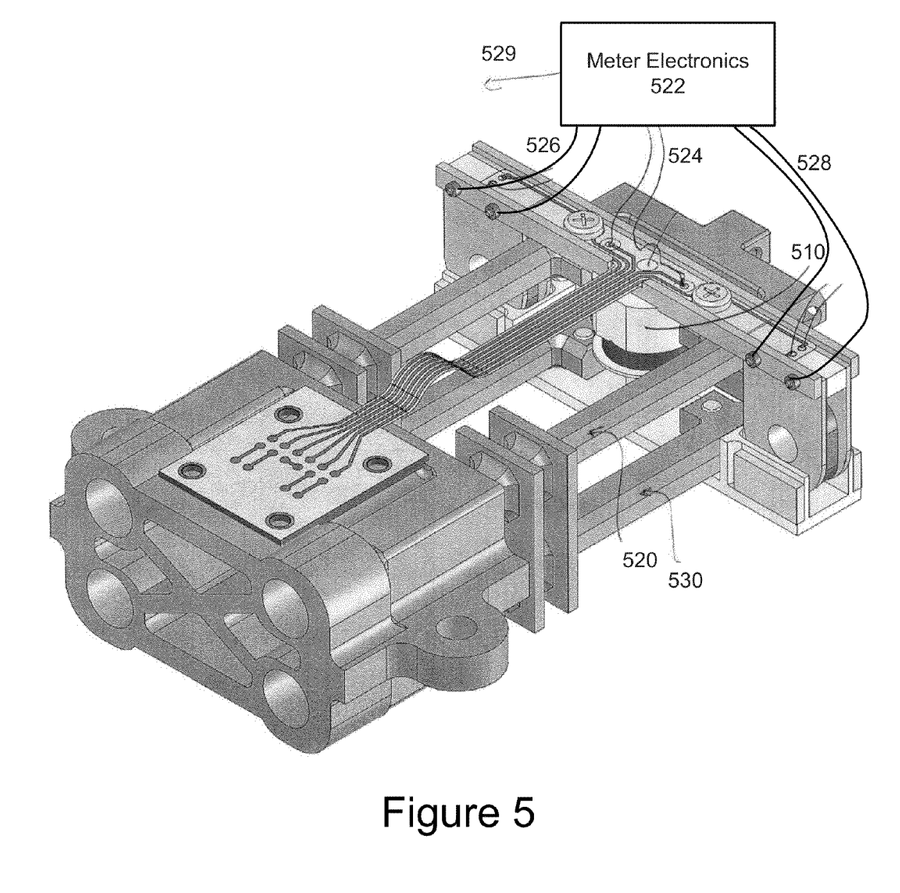
FIG. 5. Illustration of a partially assembled Coriolis flow sensor fabricated from an elastic polymeric material connected to metering electronics.

FIG. 4 discloses a magnet and coil "driver" comprised of permanent magnet 492 and coil 494 fixedly attached respectively to flow sensitive elements 420 and 430, which are caused to vibrate in phase opposition similar to the tines of a tuning fork. FIG. 5 illustrates driver coil 510 is energized by signals received from meter electronics 522 over path 524. The material flow through the vibrating flow tubes generate Coriolis forces which are detected by magnet/coil inductive "pick-offs" (or "velocity sensors") located on opposite sides of flow sensitive structures 520 and 530. These sensors generate signals responsive to the motion generated in the side legs of flow sensitive structure 520 and 530 due to flow-induced Coriolis forces. The output signals of these magnet/coil inductive sensors are transmitted over paths 526 and 528 to meter electronics 522 which processes these signals and applies output information over path 529 indicative of the fluid material flow rate.

The vibration of elements 520 and 530 in phase opposition at their natural frequency is analogous to the vibrating tines of a tuning fork and can be modeled as a damped second-order system. Neglecting dampening, the resonant frequency in the excitation (or "drive") mode wherein elements 520 and 530 are oscillated in phase opposition, $\omega_d$ is expressed as:

$$\omega_d = \sqrt{(k_d/m)}, \quad (1)$$

where the natural circular frequency $\omega_d = 2\pi f_d$, $f_d$=natural frequency in cycles/second and m=$m_{element}+m_{fluid}$ and the spring constant $k_d$ is proportional to the elastic modulus of the material in the "drive" or excitation mode. The terms $m_{element}$ and $m_{fluid}$ respectively represent the effective mass of the element 520 (or 530) and the mass of the fluid contained therein. For metal alloys (e.g., 316L stainless steel) the elastic modulus and it's variation with temperature is well-documented. However, such is not the case with elastic polymers. The variation of spring constant, k, which is necessary to properly compensate for the temperature variation of the spring constant of an elastic polymeric material with vibrating sensitive elements 520 and 530, is not documented. In particular, the elastic modulus that requires compensation is that corresponding to the twist (torsion) or Coriolis mode, $k_c$. However, from Equation (1), it can be seen that $$k_d = m\omega_d^2, \quad (2)$$

and in the twist (torsion) or "Coriolis" response mode, $$k_c = m\omega_c^2, \quad (3)$$

wherein $k_c$ is the shear modulus of the elastic polymer and can be related to $k_d$ by the Lame' constant μ as expressed in the following equation:

$$k_c = k_d/2(1+\mu) = m\omega_d^2/2(1+\mu). \quad (4)$$

Figure 6:
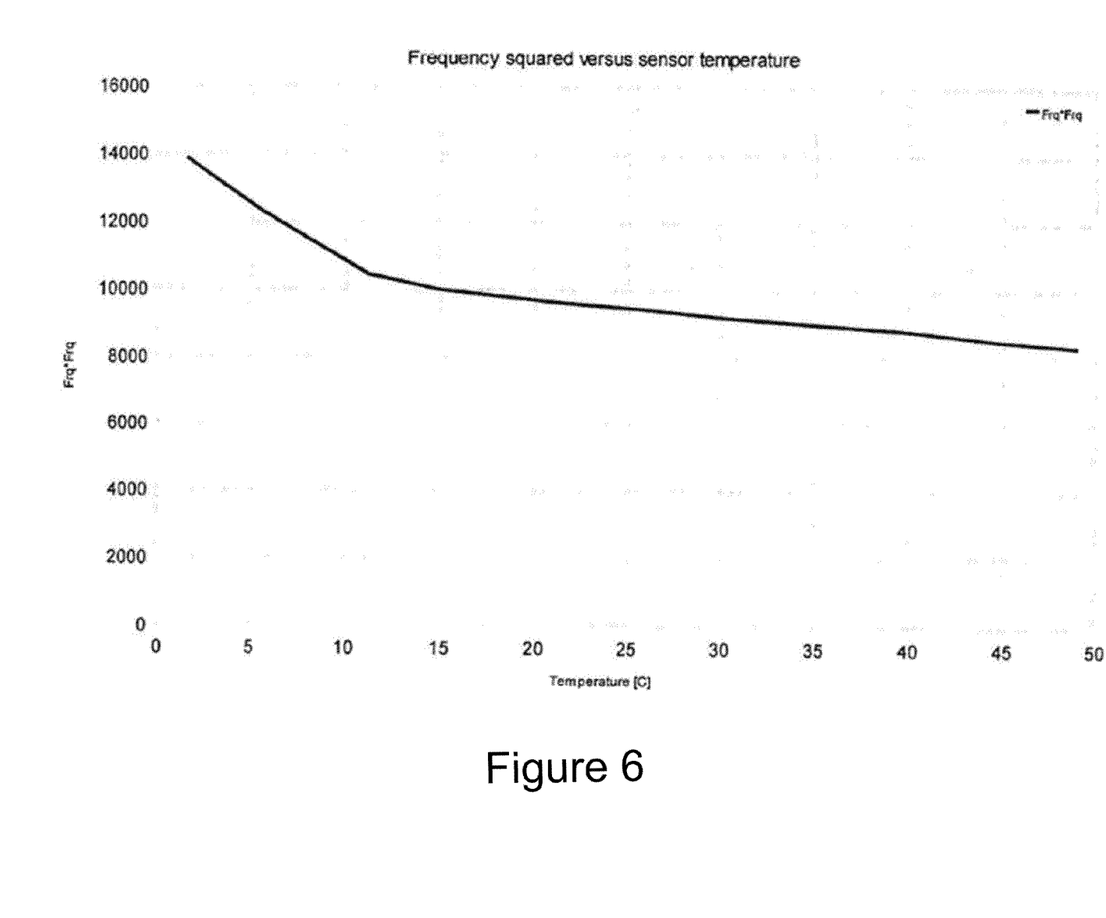
FIG. 6. Frequency vs. temperature data obtained from a Coriolis flow sensor fabricated from PFA.

Thus, measuring the variation of $w_d^2$ with temperature allows one to measure a quantity proportional to the variation of the material's shear modulus (i.e., the material's elastic modulus in the response or Coriolis mode) over a given temperature range as illustrated in FIG. 6. This consideration applies to not only elastic polymers, but any suitable elastic material including metal, ceramic, and glass materials.

Figure 7:
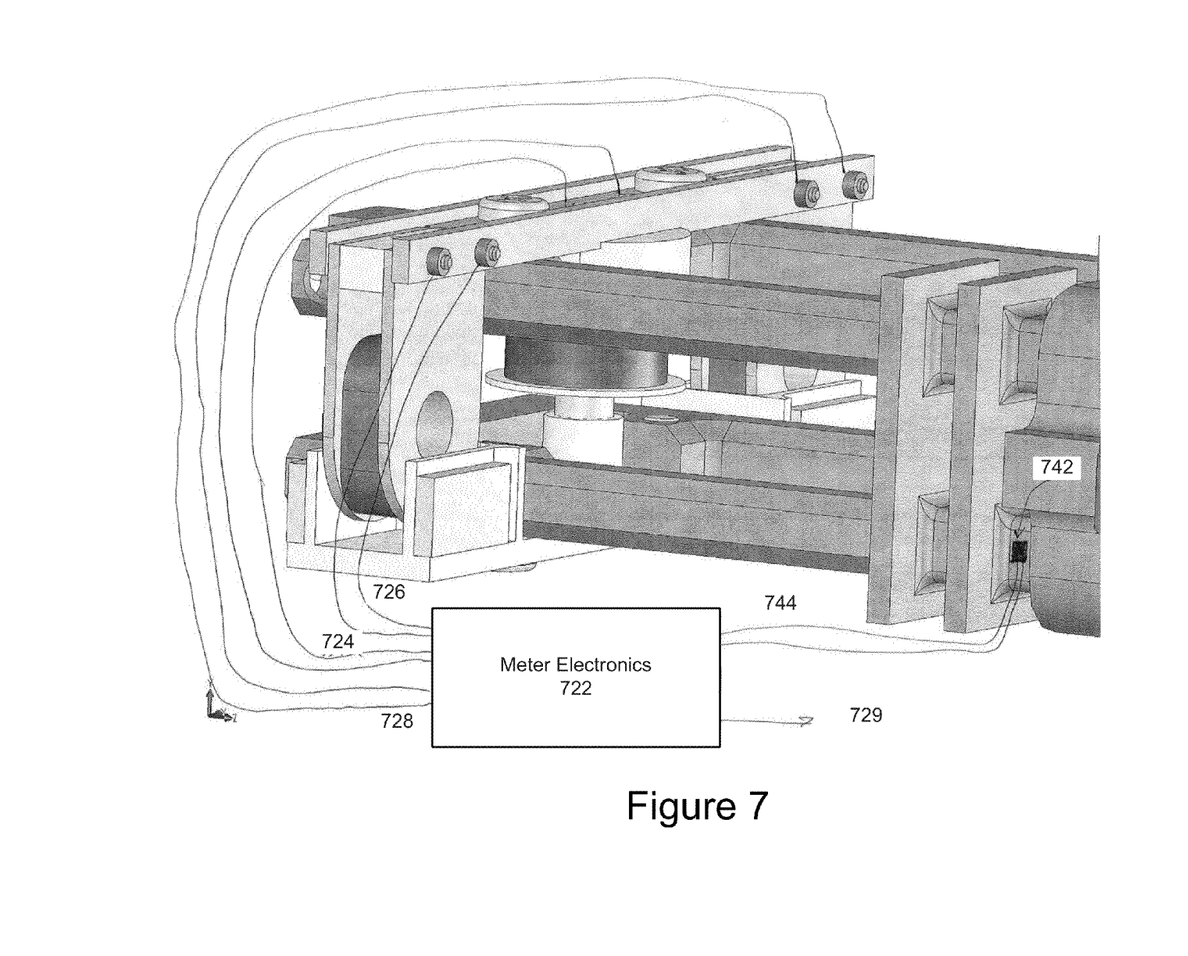
FIG. 7. Illustration of temperature sensing means bonded to the elastic polymeric material.

With reference to FIG. 7, temperature sensing means 742 is bonded to the polymeric material and communicates the temperature of the polymeric material over path 744 to meter electronics 722, according to one embodiment. Meter electronics 722 contains information proportional to $\omega_d^2$ versus temperature thereby allowing the meter electronics to properly account for the variation of the material's elastic modulus (or equivalently, the material's shear modulus) with temperature that (in combination with other factors) is a proportional factor that relates the measured signals to the fluid mass flow rate flowing through the device.

Coriolis flowmeters exhibit a flow rate indication even though no fluid is flowing through the meter. This indication is referred to as the "zero flow offset" or "Z.F.O.". One of the contributor's to Z.F.O. is a structural and/or mass imbalance from left to right causing the "U" structures to twist relative to one another as if fluid were flowing through the device. FIG. 4 illustrates two adjustment screws 495 and 496 that allow independent manual adjustment of the sensor's moment of inertia of each flow sensitive element 420 and 430 in the sensor's response mode as required in order to minimize the magnitude of the Z.F.O. with a simple screwdriver adjustment.

A mass or structural imbalance between the two "U" structures may cause the Q-factor of the oscillating structure to be lower (i.e., the "tuning fork structure" comprised of 420 and 430 may not be balanced), thereby forcing the meter electronics to deliver more energy to maintain sufficient amplitude of oscillation in order to keep the sensor's measurement sensitivity within acceptable levels. To adjust the imbalance between the two "U" structures (420 and 430), in one embodiment threaded rods with attached weights (or "nuts") 497 and 498 are added as a simple mean of adjustment to better balance the sensor's sensitive elements (420 and 430) akin to balancing the tines of tuning fork.

What is claimed is:

1. A Coriolis flowmeter, comprising:
a base comprising openings configured to allow fluid to flow through the Coriolis flowmeter;
two flow-sensitive members, each of which consists of two or more entirely straight sections, the two or more straight sections comprising flow passageways fabricated along centerlines of the straight sections for the fluid to flow through, and wherein the two flow-sensitive members are integrally connected to the base, and the two flow-sensitive members and the base are all fabricated from an elastic polymeric material, wherein each of the two flow-sensitive members comprises a component configured to allow independent manual adjustment of a moment of inertia of the flow-sensitive member for minimizing a magnitude of a zero flow offset;
two motion-responsive sensors each of which is fixedly attached to the two flow-sensitive members and configured to generate signals responsive to relative motions generated by the two flow-sensitive members due to Coriolis force induced by the fluid flowing through the Coriolis flowmeter; and
electronics communicatively connected to the two sensors and configured to receive the signals and generate output information indicative of the flow rate of the fluid that flows through the Coriolis flowmeter.

2. The Coriolis flowmeter of claim 1, wherein each of the two flow-sensitive members comprises a rectangular U-shape member, each of the rectangular U-shape members comprises a straight end-section parallel to the base and two straight side-legs integrally connecting the end section to the base.

3. The Coriolis flowmeter of claim 1, further comprising at least one isolation plate configured to establish a boundary condition for vibration of the two flow-sensitive members, wherein the two flow-sensitive members are integrally connected to the base and the at least one isolation plate, and the two flow-sensitive members, the base, and the at least one isolation plate are all fabricated from a single monolithic piece of the elastic polymeric material.

4. The Coriolis flowmeter of claim 1, wherein the two motion-responsive sensors comprise magnetic inductive sensors fixedly attached to the two flow-sensitive members.

5. The Coriolis flowmeter of claim 1, wherein the component comprises a screw.

6. The Coriolis flowmeter of claim 1, wherein each of the two flow-sensitive members comprises a threaded rod with an attached weight to allow independent manual adjustment for balancing the two flow-sensitive members.

7. The Coriolis flowmeter of claim 1, wherein the connection between the flow-sensitive members connected to the base is free of an adhesive or a mechanical joint.

8. The Coriolis flow meter of claim 1, wherein at least one flow passageway is fabricated completely through its corresponding straight section to form a first opening for connection to an opening of the base and a second opening opposite the first opening not connectable to the base.

9. A Coriolis flowmeter, comprising:
a base comprising openings configured to allow fluid to flow through the Coriolis flowmeter;
two flow-sensitive members, each of which comprises of two or more straight sections, the two or more straight sections comprising flow passageways fabricated along centerlines of the straight sections for the fluid to flow through, at least one flow passageway fabricated completely through its corresponding straight section to form a first opening for connection to an opening of the base and a second opening opposite the first opening not connectable to the base, and wherein the two flow-sensitive members are integrally connected to the base, and the two flow-sensitive members and the base are all fabricated from an elastic polymeric material, wherein each of the two flow-sensitive members comprises a component configured to allow independent manual adjustment of a moment of inertia of the flow-sensitive member for minimizing a magnitude of a zero flow offset;
two motion-responsive sensors each of which is fixedly attached to the two flow-sensitive members and configured to generate signals responsive to relative motions generated by the two flow-sensitive members due to Coriolis force induced by the fluid flowing through the Coriolis flowmeter; and
electronics communicatively connected to the two sensors and configured to receive the signals and generate output information indicative of the flow rate of the fluid that flows through the Coriolis flowmeter.

* * * * *